United States Patent [19]

Weston

[11] 4,162,252
[45] Jul. 24, 1979

[54] PROCESS FOR PREPARING 3-[(BENZAMIDOPIPERID-1-YL)ALKYL] INDOLES

[75] Inventor: George O. Weston, Havant, England

[73] Assignee: John Wyeth & Brother Limited, Maidenhead, United Kingdom

[21] Appl. No.: 772,058

[22] Filed: Feb. 28, 1977

[30] Foreign Application Priority Data

Mar. 12, 1976 [GB] United Kingdom ............... 10114/76

[51] Int. Cl.$^2$ ........................................... C07D 401/06
[52] U.S. Cl. .................................... 546/201; 546/197
[58] Field of Search ...................... 260/293.52, 293.61

[56] References Cited
PUBLICATIONS

Ellzey, S., et al., *J. Org. Chem.*, 32, 846 (1967).
Brown, H., et al., *J. Am. Chem. Soc.*, 77, 6209 (1955).
Yamada, S. et al., *Chem. and Ind.*, pp. 2169–2170 (1966).
Gaylord, N., *Reduction with Complex Metal Hydrides*, Interscience, New York, 1956, pp. 592–593.

*Primary Examiner*—Henry R. Jiles
*Assistant Examiner*—Richard A. Schwartz

[57] ABSTRACT

The invention provides a new process for preparing indoles in which a 4-acylamido-1-[3-indolyl-alylene] pyridinium compound or a corresponding tetrahydropyridine compound is reduced with alkali metal borohydride in special solvents to give a corresponding piperidine compound.

5 Claims, No Drawings

PROCESS FOR PREPARING 3-[(BENZAMIDOPIPERID-1-YL)ALKYL] INDOLES

The invention relates to a novel process for preparing indole derivatives.

Accordingly the invention provides a process for preparing compounds of general formula (III)

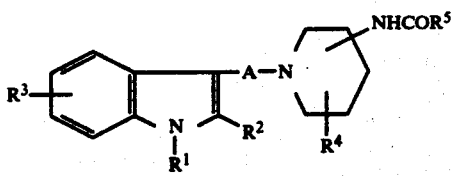

wherein $R^1$ represents hydrogen, lower alkyl, lower aralkyl or aroyl, $R^2$ represents hydrogen, lower alkyl or aryl, $R^3$ represents hydrogen, halogen, lower alkoxy, hydroxy or lower alkyl, $R^4$ represents hydrogen, halogen or lower alkyl, $R^5$ represents aryl (including heterocyclic aryl), lower alkoxy, aryloxy, lower aralkyl, lower aralkyloxy, diaryl-lower alkyl or cycloalkyl of 5 to 7 carbon atoms, and A is an alkylene radical of 1–4 carbon atoms characterised in that a compound of formula I

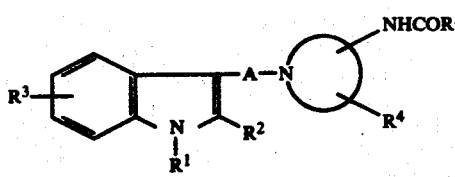

in which formula

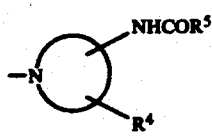

represents a ring system of general formula

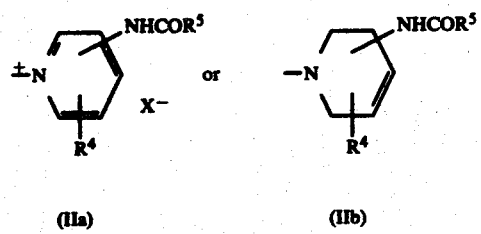

wherein A, $R^1$, $R^2$, $R^3$, $R^4$ and $R^5$ are as defined in connection with formula (III) and X is an anion, is reduced with an alkali-metal borohydride in a solvent in which the borohydride is stable and at sufficient temperature and for a time sufficient to fully reduce the ring system of formula (IIa) or (IIb), and if desired converting the product to an acid addition salt.

Preferably the solvent is an alkanol of 3 or 4 carbon atoms especially a branched chain alcohol e.g. isopropanol (bp 82.5° C.), or s-butanol. Of these isopropanol is particularly preferred.

The reduction may be carried out at a temperature in the range from 60° to 165° C., preferably 80° to 120° C. Conveniently the reduction is effected in the chosen solvent at reflux temperature.

Preferably the alkali-metal borohydride is employed in a molar ratio of from 1 mol per double bond in each mol of starting material. Thus for a starting compound containing a ring system of formula (IIa) at least 3 mols of borohydride are preferred per mol of starting material, for a starting material containing a ring system of formula (IIb), at least one mol of borohydride per mol of starting material is preferred. If desired an excess of borohydride can be used.

However, it has been found for a starting material of formula (IIa) quite good yields (e.g. of the order of 75%) can be obtained with 2 mols borohydride per mol of compound with ring system IIa. Reasonable yields are obtainable with even lesser amounts. Hence the desirable amounts are at least 0.25 mol (desirably at least 0.5 mol) borohydride per double bond for compound with ring system IIa or IIb, plus in the case of compound with ring system IIa an additional 1 mol for the quaternary salt which acts in a similar manner to a Lewis acid.

The terms "lower alkyl" and "lower alkoxy" as used herein mean the radical contains from 1 to 6, preferably 1 to 4 carbon atoms and the term "lower aralkyl" means the radical contains 7 to 10, preferably 7 to 9 carbon atoms. The "lower alkylene" group may be a branched or straight chain group, containing up to 4 carbon atoms. A is preferably the ethylene radical.

Examples of $R^1$ are hydrogen, methyl, ethyl, n-propyl, isopropyl, n-butyl, isobutyl, benzoyl and p-chlorobenzoyl. Preferably $R^1$ is a hydrogen atom. $R^2$ can be, for example, hydrogen, methyl, ethyl, n-propyl, isopropyl, n-butyl, isobutyl or substituted or unsubstituted phenyl and is preferably hydrogen or methyl. $R^3$ can be, for example, hydrogen, chlorine, methoxy, ethoxy, hydroxy, methyl, ethyl, n-propyl, isopropyl, n-butyl or isobutyl. Preferably $R^3$ is a hydrogen atom.

Examples of $R^4$ ae hydrogen, chlorine, methyl, ethyl, n-propyl, isopropyl, n-butyl or isobutyl, through preferably $R^4$ is a hydrogen atom.

$R^5$ can be, for example, phenyl, substituted phenyl (e.g. phenyl substituted by halogen such as chlorine, by alkoxy, such as methoxy or ethoxy, by alkyl such as methyl or ethyl or by methylenedioxy), heterocyclic radicals (such as 3-indolyl, 2-thienyl or 2-furyl), methoxy, ethoxy, phenoxy, benzyl, benzyloxy and diphenylmethyl.

X is preferably a halide ion such as a chloride or bromide. $R^5$ when cycloalkyl is preferably cyclohexyl.

The products of this invention are of value as pharmaceuticals as described in our U.K. Patent Specification No. 1218570 or 1273563, for instance as hypotensive or antihypertensive agents or antihistamine agents.

The process of the invention provides a convenient way of preparing indoramin, a compound first described in U.K. Patent Specification No. 1 218 570 which is now undergroing clinical trials as a hypotensive agent.

The alkali-metal borohydride may be lithium, sodium or potassium borohydride but sodium borohydride is greatly preferred.

The starting compounds of formula I are known in the literature and are particularly described for example in U.K. Patent Specification No. 1 218 570 or 1 273 563.

The process of the invention is surprising since normal borohydride reductions in methanol of a compound of formula I containing ring system (IIa) stop at a compound of formula (IIb) and it is necessary to employ catalytic hydrogenation to obtain full reduction to a compound of formula III. This process has advantages in commercial production since it avoids the necessity for catalytic hydrogenation on a plant scale. The new method also does not cause reduction of the carbonyl group of an amide link or removal of groups susceptible to hydrogenolysis such as benzyloxycarbonyl.

The invention is illustrated by the following examples.

EXAMPLE 1

3-[2-(4-Benzamido-1-piperidyl)ethyl]indole (indoramin)

A suspension of 4-benzamido-1-[2-(3-indolyl)ethyl] pyridinium bromide (4.2 g.) and sodium borohydride (1.14 g.) in isopropanol (50 ml.) was refluxed for 3½ hours. After cooling, the reaction mixture was diluted with water (50 ml.). The product was separated by filtration, washed with water then with acetone and dried to give the title compound in 82% yield, m.p. 203°–5° C.

This sample was converted to the hydrochloride m.p. 253°–6° by treatment with methanol/HCl/ethyl acetate, followed by isopropanol at reflux.

The above example is to be contrasted with Example 6 of U.K. Specification No. 1 218 570 where reduction of the same starting material with sodium borohydride in methanol gave 3-[2-(4-Benzamido-1,2,5,6,-tetrahydropyrid-1-yl)ethyl]indole.

Repetition of the above Example using sodium borohydride in refluxing ethanol also gave the tetrahydropyridine of Example 6 of U.K. Specification No. 1 210 570.

EXAMPLE 2

3-[2-(3-benzamido-1-piperidyl)ethyl]indole

Following the procedure of Example 1 above 3-benzamido-1-[2-(3-indolyl)ethyl]-pyridinium bromide upon reduction with sodium borohydride in isopropanol gives the title compound.

In contrast, treatment of this starting material with sodium borohydride in methanol gives the tetrahydropyridine (Example 7 of U.K. Specification No. 1 218 570).

EXAMPLE 3

3-[2-(4-[4-chlorobenzamido]-piperid-1-yl)-ethyl]indole 4-(4-chloro)benzamido-1-[2-(3-indolyl)ethyl]-pyridinium bromide is reduced with sodium borohydride in refluxing isopropanol according to the procedure of Example 1 to obtain the title compound.

In contrast treatment of the above pyridinium compound with sodium borohydride in methanol gives the 3[2-(4-[4-benzamido]-1,2,5,6-tetrahydropyrid-1-yl]indole—see Example 9 of U.K. Specification No. 1218570.

EXAMPLE 4

3-[2-(4-benzamido-1-piperidyl)ethyl]indole

A suspension of 4-benzamido-1-[2-(3-indolyl)ethyl]-pyridinium bromide (7.3 kg.) and sodium borohydride (2.5 kg.) in isopropanol (57 kg.) was stirred and refluxed for 6 hours. The reaction mixture was cooled to 25° and diluted with water. The product was separated by filtration and washed with aqueous methanol then with water and finally with methanol, and dried to give 4.45 kg. of the crude title compound. This was purified by dissolving in dimethylformamide (21 kg.) at 50°–60° and slowly adding water (22 kg.). After cooling, the product was separated by filtration, washed with water then with methanol, and dried to give 3.9 kg. of the title compound (65% yield).

EXAMPLE 5

3-[2-(4-benzamido-1-piperidyl)ethyl]indole

A suspension of 4-benzamido-1-[2-(3-indolyl)ethyl]-pyridinium bromide (48.7 kg.) and sodium borohydride (17.4 Kg.) in isopropanol (424 kg.) was stirred and refluxed for 6 hours. The reaction mixture was cooled to 25° and diluted with water. The product was separated by filtration and washed with aqueous methanol then with water and finally with methanol, and dried to give 40.7 kg. of the crude title compound. This was purified by dissolving in dimethylformamide (193 kg.) at 50°–60° and slowly adding water (220 kg.) to the filtered solution. After cooling, the product was separated by filtration, washed with water then with methanol, and dried to give 30.3 kg. of the title compound (75.5% yield).

EXAMPLE 6

3-[2-(4-benzamido-1-piperidyl)ethyl]indole

A suspension of 4-benzamido-1-[2-(3-indolyl)ethyl]-pyridinium bromide (10.5g) and sodium borohydride (2.8 g) in sec-butanol (100 ml) was stirred and refluxed for 6 hours. The reaction mixture was cooled to 25° and diluted with aqueous methanol. The product was separated by filtration and washed with aqueous methanol then with water and finally with methanol, and dried to give the crude title compound. This was purified as described in Example 5 to give the title compound mp 203°–5° C.

We claim:

1. A process for preparing compounds of general formula (III)

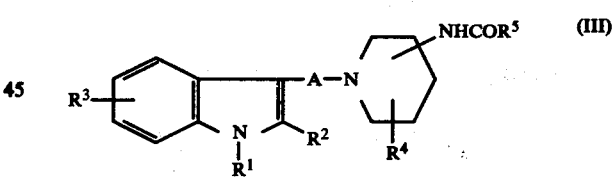

wherein $R^1$ represents hydrogen, lower alkyl, lower aralkyl or aroyl, $R^2$ represents hydrogen, lower alkyl or aryl, $R^3$ represents hydrogen, halogen, lower alkoxy, hydroxy or lower alkyl, $R^4$ represents hydrogen, halogen or lower alkyl, $R^5$ represents aryl (including heterocyclic aryl), lower alkoxy, aryloxy, lower aralkyl, lower aralkyloxy, diaryl-lower alkyl or cycloalkyl of 5 to 7 carbon atoms, and A is an alkylene radical of 1–4 carbon atoms in which a compound of formula I

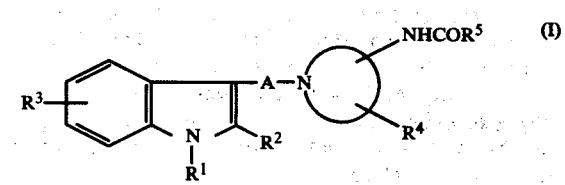

in which formula

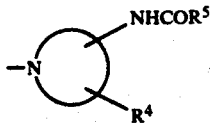

represents a ring system of general formula

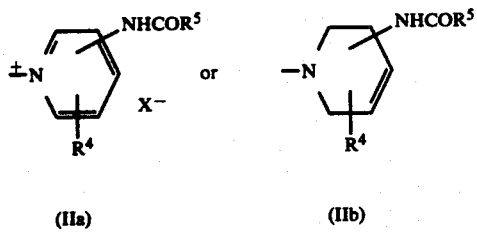

wherein A, $R^1$, $R^2$, $R^3$, $R^4$ and $R^5$ are as defind in connection with formula (III) and X is an anion, is reduced with an alkali-metal borohydride in a solvent selected from alkanols of 3–4 carbon atoms, glycol ethers or dioxane, and if desired converting the product to an acid addition salt.

2. A process as claimed in claim 1, wherein the solvent is isopropanol.

3. A process as claimed in claim 2, wherein the reduction is carried out at a temperature from 80° to 120° C.

4. A process as claimed in claim 1, characterised in that a compound of formula III wherein $R^1$, $R^2$, $R^3$ and $R^4$ are hydrogen and $R^5$ is phenyl, or cyclohexyl is reduced to a corresponding compound of formula I.

5. A process wherein a 4-benzamido-1-[2-(3-indolyl)ethyl]pyridinium halide is reduced with an alkali-metal borohydide in a solvent selected from isopropanol and s. butanol to give 3-[2-(4-benzamido-1-piperidyl)ethyl]indole.

* * * * *

UNITED STATES PATENT AND TRADEMARK OFFICE
CERTIFICATE OF CORRECTION

PATENT NO. : 4,162,252
DATED : July 24, 1979
INVENTOR(S) : George O. Weston

It is certified that error appears in the above-identified patent and that said Letters Patent are hereby corrected as shown below:

| | |
|---|---|
| Abstract | Line 2, "alylene" should read - -alkylene- - |
| Column 2, | line 32, - -benzyl- - should be after "isobutyl" |
| | line 40, "ae" should read - -are- - |
| | line 59, "undergroing" should read - -undergoing- - |
| Column 3, | line 34, "210" should read - -218- - |
| Column 6, | line 1, "defind" should read - -defined- - |
| Column 6, | lines 4-6 should read - -from isopropanol and s-butanol- - |
| Column 6, | lines 11/12, "characterised in that" should read - -wherein- - |
| Column 6, | line 12, "formula III" should read - -formula I- - |
| Column 6, | line 14, "formula I " should read - -formula III- - |

Signed and Sealed this

Ninth Day of September 1980

[SEAL]

Attest:

SIDNEY A. DIAMOND

Attesting Officer

Commissioner of Patents and Trademarks